(12) United States Patent
Boutell et al.

(10) Patent No.: US 11,667,953 B2
(45) Date of Patent: Jun. 6, 2023

(54) METHODS AND COMPOSITIONS FOR CLUSTER GENERATION BY BRIDGE AMPLIFICATION

(71) Applicant: Illumina Cambridge Limited, Cambridge (GB)

(72) Inventors: Jonathan Mark Boutell, Cambridge (GB); Oliver Miller, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 642 days.

(21) Appl. No.: 16/702,169

(22) Filed: Dec. 3, 2019

(65) Prior Publication Data

US 2020/0181686 A1 Jun. 11, 2020

Related U.S. Application Data

(60) Provisional application No. 62/775,679, filed on Dec. 5, 2018.

(51) Int. Cl.
| | | |
|---|---|---|
| *C12Q 1/6806* | (2018.01) | |
| *C12N 9/22* | (2006.01) | |
| *C12Q 1/6874* | (2018.01) | |
| *C12Q 1/6844* | (2018.01) | |

(52) U.S. Cl.
CPC ............. *C12Q 1/6806* (2013.01); *C12N 9/22* (2013.01); *C12Q 1/6844* (2013.01); *C12Q 1/6874* (2013.01); *C12N 2800/80* (2013.01)

(58) Field of Classification Search
CPC .. C12Q 1/6806; C12Q 1/6844; C12Q 1/6874; C12Q 2565/543; C12N 9/22; C12N 2800/80; C12Y 301/11; C12Y 301/21; C12Y 302/02027
See application file for complete search history.

(56) References Cited

U.S. PATENT DOCUMENTS

| | | |
|---|---|---|
| 7,754,429 B2 | 7/2010 | Rigatti et al. |
| 7,790,418 B2 | 9/2010 | Mayer |
| 8,017,335 B2 | 9/2011 | Smith |
| 8,143,008 B2 | 3/2012 | Kawashima et al. |
| 8,192,930 B2 | 6/2012 | Vermaas et al. |
| 9,029,103 B2 | 5/2015 | Rigatti et al. |
| 9,139,874 B2 | 9/2015 | Myers et al. |
| 9,453,258 B2 | 9/2016 | Kain et al. |
| 2004/0057917 A1 | 3/2004 | Wolf et al. |
| 2010/0035269 A1 | 2/2010 | Ma et al. |
| 2010/0129874 A1* | 5/2010 | Mitra ...................... C12P 19/34 435/91.2 |
| 2012/0156728 A1 | 6/2012 | Li Bin et al. |
| 2013/0012399 A1* | 1/2013 | Myers .................. C12Q 1/6806 435/6.1 |
| 2020/0181686 A1 | 6/2020 | Boutell et al. |
| 2020/0190578 A1 | 6/2020 | Boutell et al. |

FOREIGN PATENT DOCUMENTS

| | | |
|---|---|---|
| DE | 19812103 | 9/1999 |
| EP | 3260554 | 12/2017 |
| WO | 20070010251 | 1/2007 |
| WO | 2014031163 A1 | 2/2014 |
| WO | 2016075204 | 5/2016 |

OTHER PUBLICATIONS

International Preliminary Report on Patentability for PCT/EP2019/083173, dated Jun. 21, 2021, 7 pages.
International Search Report and Written Opinion for PCT/EP2019/083173, issued by the European Patent Office, 14 pgs.
Lehman and Nussbaum, "The Deoxyribonucleases of *Escherichia coli*, V. On the Specificity of Exonuclease I (Phosphodiesterase)," Journal of Biological Chem, Aug. 1054;239(8): 2628-2636.
International Search Report and Written Opinion for PCT/EP2019/084183, issued by the European Patent Office, dated Feb. 21, 2020; 14 pgs.
Ma et al., "Isothermal amplification method for next-generation sequencing," PNAS, Aug. 27, 2013; 110(35):14320-14323.
Ma et al., "WildFire: A Simple Monoclonal Colony Generation Technology without Emulsion PCR," LifeTechnologies, 2012, [Online] obtained May 12, 2012 at http://assets.thermofisher.com/TFS-Assets/LSG/brochures/5500-wildfire-ashg-poster.pdf.

* cited by examiner

*Primary Examiner* — David C Thomas
(74) *Attorney, Agent, or Firm* — Mueting Raasch Group

(57) ABSTRACT

The present disclosure is concerned with compositions and methods for reducing the steps used in the generation of monoclonal clusters by combining the enzymes used for linearization and removal of unused surface primers.

7 Claims, 3 Drawing Sheets

METHODS AND COMPOSITIONS FOR CLUSTER GENERATION BY BRIDGE AMPLIFICATION

CROSS-REFERENCE TO RELATED APPLICATIONS

This application claims the benefit of U.S. Provisional Application No. 62/775,679, filed Dec. 5, 2018, the disclosure of which is incorporated by reference herein in its entirety.

FIELD

The present disclosure relates to, among other things, the amplification of target nucleic acids to generate clusters of amplicons for sequencing, particularly in the context of reducing the steps involved in obtaining sequence information from a sample.

BACKGROUND

Next-generation sequencing (NGS) technology relies on the highly parallel sequencing of monoclonal populations of amplicons that were produced from a single target nucleic acid. NGS methods have greatly increased sequencing speed and data output, resulting in the massive sample throughput of current sequencing platforms. Further reduction of the time for sequencing a template is highly desirable, but it is necessary to maintain useful signal-to-noise ratios, intensity, and increased percentage of clusters that pass filter, all of which contribute to increased data output and data quality. Reducing the time for sequencing a template can be achieved by combining separate steps; however, separate steps often cannot be combined due to incompatibilities. For instance, the activity of a one enzyme can be inhibited by the product of another enzyme, therefore requiring the use of the enzymes in separate steps.

SUMMARY OF THE APPLICATION

Next generation sequencing (NGS) technology relies on the highly parallel sequencing of monoclonal populations of amplicons that were produced from a single target nucleic acid. Multiple steps are required for producing the monoclonal populations of amplicons and for sequencing, and each step adds to the overall time required before useful sequence data can be obtained for a sample. For instance, multiple steps are necessary for producing the monoclonal populations of amplicons, including attaching and then amplifying target nucleic acids present at amplification sites of an array. The inventors have discovered that two separate steps used in the production of monoclonal amplicons can be combined. In standard routine methods, during production of monoclonal amplicons the amplification sites are treated with an exonuclease, and then treated in a separate step with glycosylase enzymes that selectively produce a single nucleotide gap at a predetermined location. The steps are performed in that order because producing the single nucleotide gap also produces a structure, a 3'-phosphate, that inhibits the activity of the exonuclease. Unexpectedly, the inventors discovered that the exonuclease and glycosylases could be combined into one step with little to no detrimental effect on primary metrics, read quality, dual indexing, or genome build metrics. This results in faster sequencing as two steps are now performed at the same time. It also has the advantage of reducing the number and amounts of reagents, thereby reducing overall cost to the consumer.

Provided herein are compositions. In one embodiment, a composition includes a uracil DNA glycosylase, an endonuclease, and an exonuclease having a 3' to 5' single-stranded DNA exonuclease activity.

Also provided are methods. In one embodiment, a method is for preparing nucleic acids for a sequencing reaction. The method includes providing an array having a plurality of amplification sites. The amplification sites include a plurality of capture nucleic acids attached to the amplification sites, wherein a first population of the plurality of capture nucleic acids includes a cleavage site. The amplification sites also include a plurality of clonal double-stranded modified target nucleic acids, wherein both strands of each double-stranded target nucleic acid are attached at their 5' ends to a capture nucleic acid, wherein one strand is attached to a capture nucleic acid that includes the cleavage site, and wherein the cleavage site is positioned in a double-stranded region of each double-stranded molecule. The method also includes contacting the array with a composition that includes at least one enzyme to produce an abasic site at the cleavage site and an exonuclease having a 3' to 5' single-stranded DNA exonuclease activity, wherein cleavage occurs at the cleavage site, wherein cleavage converts one strand of double-stranded target nucleic acids into a first strand attached to the amplification site and a second strand that is not attached to the amplification site, and wherein single-stranded capture nucleic acids comprising a free 3' end are reduced in length by the exonuclease.

Definitions

Terms used herein will be understood to take on their ordinary meaning in the relevant art unless specified otherwise. Several terms used herein and their meanings are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, e.g., a target nucleic acid or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a polymerase extension product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material, e.g., amplicons derived from a target nucleic acid, that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule, or moiety thereof that is capable of attaching, retaining, or binding to a target molecule (e.g. a target nucleic acid). Exemplary capture agents include, without limitation, a capture nucleic acid that is complementary to at least a portion of a modified target nucleic acid (e.g., a universal capture binding sequence), a member of a receptor-ligand binding pair (e.g. avidin, streptavidin, biotin, lectin, carbohydrate, nucleic acid binding protein, epitope, antibody, etc.) capable of binding to a modified target nucleic acid (or linking moiety attached thereto), or a chemical reagent capable of forming a covalent bond with a modified target nucleic acid (or linking moiety attached thereto). In one embodiment, a capture agent is a nucleic acid. A nucleic acid capture agent can also be used as an amplification primer.

The terms "P5" and "P7" may be used when referring to a nucleic acid capture agent. The terms "P5'" (P5 prime) and "P7'" (P7 prime) refer to the complement of P5 and P7, respectively. It will be understood that any suitable nucleic acid capture agent can be used in the methods presented herein, and that the use of P5 and P7 are exemplary embodiments only. Uses of nucleic acid capture agents such as P5 and P7 on flowcells is known in the art, as exemplified by the disclosures of WO 2007/010251, WO 2006/064199, WO 2005/065814, WO 2015/106941, WO 1998/044151, and WO 2000/018957. One of skill in the art will recognize that a nucleic acid capture agent can also function as an amplification primer. For example, any suitable nucleic acid capture agent can act as a forward amplification primer, whether immobilized or in solution, and can be useful in the methods presented herein for hybridization to a sequence (e.g., a universal capture binding sequence) and amplification of a sequence. Similarly, any suitable nucleic acid capture agent can act as a reverse amplification primer, whether immobilized or in solution, and can be useful in the methods presented herein for hybridization to a sequence (e.g., a universal capture binding sequence) and amplification of a sequence. In view of the general knowledge available and the teachings of the present disclosure, one of skill in the art will understand how to design and use sequences that are suitable for capture and amplification of target nucleic acids as presented herein.

As used herein, the term "universal sequence" refers to a region of sequence that is common to two or more target nucleic acids, where the molecules also have regions of sequence that differ from each other. A universal sequence that is present in different members of a collection of molecules can allow capture of multiple different nucleic acids using a population of capture nucleic acids that are complementary to a portion of the universal sequence, e.g., a universal capture binding sequence. Non-limiting examples of universal capture binding sequences include sequences that are identical to or complementary to P5 and P7 primers. Similarly, a universal sequence present in different members of a collection of molecules can allow the replication or amplification of multiple different nucleic acids using a population of universal primers that are complementary to a portion of the universal sequence, e.g., a universal primer binding site. Target nucleic acid molecules may be modified to attach universal adapters (also referred to herein as adapters), for example, at one or both ends of the different target sequences, as described herein.

As used herein, the term "adapter" and its derivatives, e.g., universal adapter, refers generally to any linear oligonucleotide which can be ligated to a target nucleic acid. In some embodiments, the adapter is substantially non-complementary to the 3' end or the 5' end of any target sequence present in a sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a capture nucleic acid. In some embodiments, the adapter can include a barcode, also referred to as an index or tag, to assist with downstream error correction, identification, or sequencing. The terms "adaptor" and "adapter" are used interchangeably.

As defined herein, "sample" and its derivatives is used in its broadest sense and includes any specimen, culture and the like that is suspected of including a target nucleic acid. In some embodiments, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

As used herein, the terms "clonal population" and "monoclonal population" are used interchangeably and refer to a population of nucleic acids that is homogeneous with respect to a particular nucleotide sequence. The homogenous sequence is typically at least 10 nucleotides long, but can be even longer including for example, at least 50, at least 100, at least 250, at least 500, or at least 1000 nucleotides long. A clonal population can be derived from a single target nucleic acid. Typically, all of the nucleic acids in a clonal population will have the same nucleotide sequence. It will be understood that a small number of mutations (e.g. due to amplification artifacts) can occur in a clonal population without departing from clonality. It will also be understood that a small number of different target nucleic acid (e.g., due to a target nucleic acid that was not amplified or amplified to a limited degree) can occur in a clonal population without departing from clonality.

As used herein, the term "different," when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other. As used herein, the term "different," when used in reference to amplification sites, means that the amplification sites are present at distinct separate locations on the same array.

As used herein, the term "fluidic access," when used in reference to a molecule in a fluid and a site in contact with the fluid, refers to the ability of the molecule to move in or through the fluid to contact or enter the site. The term can also refer to the ability of the molecule to separate from or exit the site to enter the solution. Fluidic access can occur when there are no barriers that prevent the molecule from entering the site, contacting the site, separating from the site and/or exiting the site. However, fluidic access is understood to exist even if diffusion is retarded, reduced or altered so long as access is not absolutely prevented.

As used herein, the term "double stranded," when used in reference to a nucleic acid molecule, means that substantially all of the nucleotides in the nucleic acid molecule are hydrogen bonded to a complementary nucleotide. A partially double stranded nucleic acid can have at least 10%, at least 25%, at least 50%, at least 60%, at least 70%, at least 80%, at least 90% or at least 95% of its nucleotides hydrogen bonded to a complementary nucleotide.

As used herein, the term "each," when used in reference to a collection of items, is intended to identify an individual item in the collection but does not necessarily refer to every item in the collection unless the context clearly dictates other.

As used herein, the term "excluded volume" refers to the volume of space occupied by a particular molecule to the exclusion of other such molecules.

As used herein, the term "interstitial region" refers to an area in a substrate or on a surface that separates other areas of the substrate or surface. For example, an interstitial region can separate one feature of an array from another feature of the array. The two regions that are separated from each other can be discrete, lacking contact with each other. In another example, an interstitial region can separate a first portion of a feature from a second portion of a feature. The separation provided by an interstitial region can be partial or full separation. Interstitial regions will typically have a surface material that differs from the surface material of the features on the surface. For example, features of an array can have an amount or concentration of capture agents that exceeds the amount or concentration present at the interstitial regions. In some embodiments the capture agents may not be present at the interstitial regions.

As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. As described in detail herein, polymerases can be used during an amplification to produce clonal clusters, can be used during a sequencing reaction to determine the sequence of a nucleic acid, and different polymerases can be used in each of these aspects. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bsu (*Bacillus subtilis*), Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "nucleic acid" is intended to be consistent with its use in the art and includes naturally occurring nucleic acids and functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from adenine, thymine, cytosine or guanine and a ribonucleic acid can have one or more bases selected from uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid having a universal sequence at each end, for instance a universal adapter at each end, can be referred to as a modified target nucleic acid.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, the term "rate," when used in reference to transport, amplification, capture or other chemical processes, is intended to be consistent with its meaning in chemical kinetics and biochemical kinetics. Rates for two processes can be compared with respect to maximum rates (e.g. at saturation), pre-steady state rates (e.g. prior to equilibrium), kinetic rate constants, or other measures known in the art. In particular embodiments, a rate for a particular process can be determined with respect to the total time for completion of the process. For example, an amplification rate can be determined with respect to the time taken for amplification to be complete. However, a rate for a particular process need not be determined with respect to the total time for completion of the process.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Conditions that are "suitable" for an event to occur, such as exonuclease-mediated digestion of a nucleic acid, or "suitable" conditions are conditions that do not prevent such events from occurring. Thus, these conditions permit, enhance, facilitate, and/or are conducive to the event.

As used herein, "providing" in the context of a composition, an article, or a nucleic acid, means making the composition, article, or nucleic acid, purchasing the composition, article, or nucleic acid, or otherwise obtaining the compound, composition, article, nucleic acid.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Presented herein are methods and compositions related to sequencing nucleic acids. The present disclosure provides methods including preparing nucleic acids for a sequencing reaction, generating clonal clusters, and fabricating an array of nucleic acids on a surface. In one embodiment, a method includes providing an array that includes a plurality of amplification sites. Each amplification site includes a plurality of double-stranded amplicons. For instance, in FIG. 1A an amplification site 10 is shown with one member of a plurality of double-stranded amplicons 11.

Figure 1A:
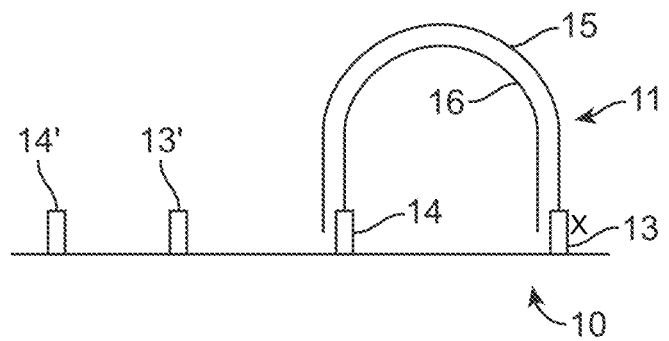
FIGS. 1A-1D show schematic drawings of an embodiment of preparing a nucleic acid for sequencing according to various aspects of the disclosure presented herein.

A plurality of capture nucleic acids is attached to the surface of the amplification site. At least two populations of capture nucleic acids is present, and in some embodiments three or more populations are present. At least one population of the capture nucleic acids includes a cleavage site. In one embodiment, the cleavage site includes a uracil residue. Each double-stranded amplicon molecule is in a bridged structure, where they are attached at their 5' ends to a capture nucleic acid and not attached to the array at their 3' ends. The cleavage site is positioned in a double-stranded region of each double-stranded molecule. For instance, as shown in FIG. 1A two populations of capture nucleic acids are shown. One population is shown either attached 13 at one end of each amplicon or bound 13' to the surface of the amplification site 10 but not attached to an amplicon 11. A second population of capture nucleic acids is also shown either attached 14 at the other end of each amplicon or bound 14' to the surface of the amplification site 10 but not attached to an amplicon 11. Also shown in FIG. 1A is the cleavage site (marked with an X on capture nucleic acid 13).

Figure 1B:
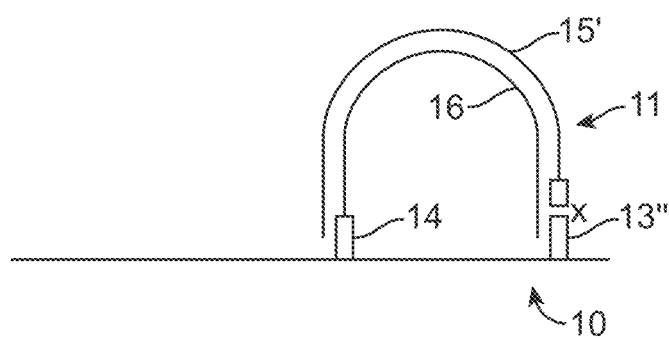

The method further includes contacting the amplification sites of the array with an enzyme that cleaves one DNA strand at the cleavage site, and an exonuclease having a 3' to 5' single-stranded DNA exonuclease activity. The exonuclease acts to digest single-stranded capture nucleic acids comprising a free 3'-OH end. For instance, as shown in FIG. 1B, the cleavage site X in the amplicon 11 is cleaved leaving a shortened capture nucleic acid 13". The unattached capture nucleic acids 13' and 14' are no longer present at the amplification site 10.

In one embodiment, the sequence of the attached strand can be determined by using a DNA polymerase with strand displacing activity, where the 3' end of the shortened capture nucleic acid (13" in FIG. 1B) is used as the primer for the initiation of DNA synthesis. In some embodiments the enzyme that cleaves one DNA strand at the cleavage site will modify the 3' end of the shortened capture nucleic acid to terminate in a 3'-phosphate. The 3'-phosphate can be removed by a phosphatase before beginning the sequencing reaction.

Figure 1C:
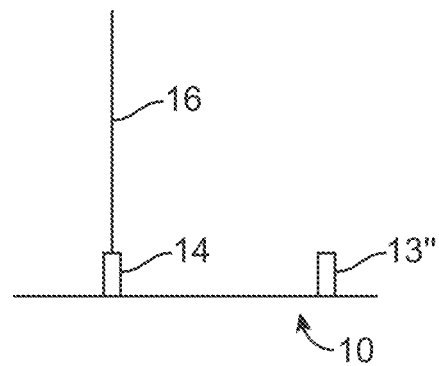

Instead of sequencing the attached strand, the method can also include subjecting the cleaved double-stranded amplicons to denaturing conditions to remove the portion of the cleaved strand (15' in FIG. 1B) not attached to the array. This results in immobilized single-stranded nucleic acids. For instance, as shown in FIG. 1C, the DNA stand that is unattached is no longer hybridized to the attached strand 16 and has been lost.

Figure 1D:
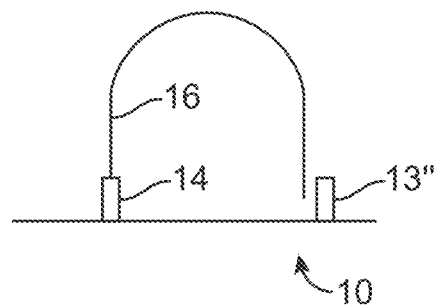

In one embodiment, the immobilized single-stranded nucleic acids can be re-annealed to the shortened capture nucleic acid 13". For instance, as shown in FIG. 1D, the attached DNA stand 16 is re-annealed to the shortened capture nucleic acid 13".

Arrays

An array of amplification sites used in a method set forth herein can be present as one or more substrates. Exemplary types of substrate materials that can be used for an array include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™ Exemplary silica-based materials include silicon and various forms of modified silicon.

In particular embodiments, a substrate can be within or part of a vessel such as a well, tube, channel, cuvette, Petri plate, bottle, or the like. A particularly useful vessel is a flow-cell, for example, as described in U.S. Pat. No. 8,241,573 or Bentley et al., Nature 456:53-59 (2008). Exemplary flow-cells are those that are commercially available from Illumina, Inc. (San Diego, Calif.). Another particularly useful vessel is a well in a multiwell plate or microtiter plate.

In some embodiments, the amplification sites of an array can be configured as features on a surface. The features can be present in any of a variety of desired formats. For example, the sites can be wells, pits, channels, ridges, raised regions, pegs, posts or the like. In one embodiment, the amplification sites can contain beads. However, in particular embodiments the sites need not contain a bead or particle. Exemplary sites include wells that are present in substrates used for commercial sequencing platforms sold by 454 LifeSciences (a subsidiary of Roche, Basel Switzerland) or Ion Torrent (a subsidiary of Life Technologies, Carlsbad, Calif., USA). Other substrates having wells include, for example, etched fiber optics and other substrates described in U.S. Pat. Nos. 6,266,459; 6,355,431; 6,770,441; 6,859,570; 6,210,891; 6,258,568; 6,274,320; 8,262,900; 7,948,015; U.S. Pat. Pub. No. 2010/0137143; U.S. Pat. No. 8,349,167, or PCT Publication No. WO 00/63437. In several cases the substrates are exemplified in these references for applications that use beads in the wells. The well-containing substrates can be used with or without beads in the methods or compositions of the present disclosure. In some embodiments, wells of a substrate can include gel material (with or without beads) as set forth in U.S. Pat. No. 9,512,422.

The amplification sites of an array can be metal features on a non-metallic surface such as glass, plastic or other materials exemplified herein. A metal layer can be deposited on a surface using methods known in the art such as wet plasma etching, dry plasma etching, atomic layer deposition, ion beam etching, chemical vapor deposition, vacuum sputtering, or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, Ann. Rev. Mater. Sci. 7:239-60 (1977). Metal layer deposition techniques, such as those exemplified herein, can be combined with photolithography techniques to create metal regions or patches on a surface. Exemplary methods for combining metal layer deposition techniques and photolithography techniques are provided in U.S. Pat. Nos. 8,778,848 and 8,895,249.

An array of features can appear as a grid of spots or patches. The features can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features. In particular embodiments, features of an array can each have an area that is larger than about 100 $nm^2$, 250 $nm^2$, 500 $nm^2$, 1 $\mu m^2$, 2.5 $\mu m^2$, 5 $\mu m^2$, 10 $\mu m^2$, 100 $\mu m^2$, or 500 $\mu m^2$. Alternatively or additionally, features of an array can each have an area that is smaller than about 1 $mm^2$, 500 $\mu m^2$, 100 $\mu m^2$, 25 $\mu m^2$, 10 $\mu m^2$, 5 $\mu m^2$, 1 $\mu m^2$, 500 $nm^2$, or 100 $nm^2$.

Indeed, a region can have a size that is in a range between an upper and lower limit selected from those exemplified above.

For embodiments that include an array of features on a surface, the features can be discrete, being separated by interstitial regions. The size of the features and/or spacing between the regions can vary such that arrays can be high density, medium density, or lower density. High density arrays are characterized as having regions separated by less than about 15 μm. Medium density arrays have regions separated by about 15 to 30 μm, while low density arrays have regions separated by greater than 30 μm. An array useful in the disclosure can have regions that are separated by less than 100 μm, 50 μm, 10 μm, 5 μm, 1 μm, or 0.5 μm.

In particular embodiments, an array can include a collection of beads or other particles. The particles can be suspended in a solution or they can be located on the surface of a substrate. Examples of bead arrays in solution are those commercialized by Luminex (Austin, Tex., USA). Examples of arrays having beads located on a surface include those wherein beads are located in wells such as a BeadChip array (Illumina Inc., San Diego, Calif., USA) or substrates used in sequencing platforms from 454 LifeSciences (a subsidiary of Roche, Basel, Switzerland) or Ion Torrent (a subsidiary of Life Technologies, Carlsbad, Calif. USA). Other arrays having beads located on a surface are described in U.S. Pat. Nos. 6,266,459; 6,355,431; 6,770,441; 6,859,570; 6,210,891; 6,258,568; 6,274,320; U.S. Pat. Pub. No. 2009/0026082 A1; U.S. Pat. Pub. No. 2009/0127589 A1; U.S. Pat. Pub. No. 2010/0137143 A1; U.S. Pat. Pub. No. 2010/0282617 A1; or PCT Publication No. WO 00/63437. Several of the above references describe methods for attaching target nucleic acids to beads prior to loading the beads in or on an array substrate. It will be understood, however, that the beads can be made to include amplification primers and the beads can then be used to load an array, thereby forming amplification sites for use in a method set forth herein. As set forth previously herein, the substrates can be used without beads. For example, amplification primers can be attached directly to the wells or to gel material in wells. Thus, the references are illustrative of materials, compositions or apparatus that can be modified for use in the methods and compositions set forth herein.

Amplification sites of an array can include a plurality of capture agents capable of binding to target nucleic acids. In one embodiment, a capture agent includes a capture nucleic acid. The nucleotide sequence of the capture nucleic acid is complementary to a universal sequence of the target nucleic acids. In some embodiments, the capture nucleic acid can also function as a primer for amplification of the target nucleic acid. In some embodiments, one population of capture nucleic acid includes a P5 primer or the complement thereof. In some embodiments, the amplification sites also include a plurality of a second capture nucleic acid, and this second capture nucleic acid can include a P7 primer or the complement thereof. In some embodiments a capture nucleic acid can include a cleavage site. Cleavage sites in a capture nucleic acid are described in greater detail herein.

In particular embodiments, a capture agent, such as a capture nucleic acid, can be attached to the amplification sites. For example, the capture agent can be attached to the surface of a feature of an array. The attachment can be via an intermediate structure such as a bead, particle or gel. An example of attachment of capture nucleic acids to an array via a gel is described in U.S. Pat. No. 8,895,249 and further exemplified by flow cells available commercially from Illumina Inc. (San Diego, Calif., USA) or described in WO 2008/093098. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1) or PAZAM (see, for example, U.S. Prov. Pat. App. Ser. No. 61/753,833 and U.S. Pat. No. 9,012,022). Attachment via a bead can be achieved as exemplified in the description and cited references set forth previously herein.

In some embodiments, the features on the surface of an array substrate are non-contiguous, being separated by interstitial regions of the surface. Interstitial regions that have a substantially lower quantity or concentration of capture agents, compared to the features of the array, are advantageous. Interstitial regions that lack capture agents are particularly advantageous. For example, a relatively small amount or absence of capture moieties at the interstitial regions favors localization of target nucleic acids, and subsequently generated clusters, to desired features. In particular embodiments, the features can be concave features in a surface (e.g. wells) and the features can contain a gel material. The gel-containing features can be separated from each other by interstitial regions on the surface where the gel is substantially absent or, if present the gel is substantially incapable of supporting localization of nucleic acids. Methods and compositions for making and using substrates having gel containing features, such as wells, are set forth in U.S. Prov. App. No. 61/769,289.

Target Nucleic Acids

An array used in a method described herein includes double-stranded modified target nucleic acids. The terms "target nucleic acid," "target fragment," "target nucleic acid fragment, "target molecule," and "target nucleic acid molecule" are used interchangeably to refer to nucleic acid molecules where identification of its nucleotide sequence is desired. The target nucleic acid may be essentially any nucleic acid of known or unknown sequence. It may be, for example, a fragment of genomic DNA or cDNA. Sequencing may result in determination of the sequence of the whole or a part of the target molecule. The targets can be derived from a primary nucleic acid sample that has been randomly fragmented. In one embodiment, the targets can be processed into templates suitable for amplification by the placement of universal amplification sequences, e.g., sequences present in a universal adaptor, at the ends of each target fragment. A target nucleic acid having a universal adapter at each end can be referred to as a "modified target nucleic acid." Universal adapters are detailed herein.

The primary nucleic acid sample may originate in double-stranded DNA (dsDNA) form (e.g. genomic DNA fragments, PCR and amplification products and the like) from a sample or may originate in single-stranded form from a sample, as DNA or RNA, and been converted to dsDNA form. By way of example, mRNA molecules may be copied into double-stranded cDNAs suitable for use in a method described herein using standard techniques well known in the art. The precise sequence of the polynucleotide molecules from a primary nucleic acid sample is generally not material to the disclosure, and may be known or unknown.

In one embodiment, the primary polynucleotide molecules from a primary nucleic acid sample are DNA molecules. More particularly, the primary polynucleotide molecules represent the entire genetic complement of an organism, and are genomic DNA molecules which include both intron and exon sequences, as well as non-coding regulatory sequences such as promoter and enhancer sequences. In one embodiment, particular subsets of polynucleotide sequences or genomic DNA can be used, such as, for example, particular chromosomes. Yet more particularly, the sequence of the primary polynucleotide molecules is not known. Still yet more particularly, the primary polynucleotide molecules are human genomic DNA molecules. The DNA target fragments may be treated chemically or enzymatically either prior or subsequent to any random fragmentation processes, and prior or subsequent to the ligation of the universal adapter sequences.

The nucleic acid sample can include high molecular weight material such as genomic DNA (gDNA). The sample can include low molecular weight material such as nucleic acid molecules obtained from formalin-fixed paraffin-embedded or archived DNA samples. In another embodiment, low molecular weight material includes enzymatically or mechanically fragmented DNA. The sample can include cell-free circulating DNA. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include nucleic acid molecules obtained from an animal such as a human or mammalian source. In another embodiment, the sample can include nucleic acid molecules obtained from a non-mammalian source such as a plant, a bacterium, a virus, or a fungus. In some embodiments, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, from a missing persons DNA database, from a laboratory associated with a forensic investigation, or from forensic samples obtained by law enforcement agencies, one or more military services, or any such personnel. The nucleic acid sample may be a purified sample or a crude DNA containing lysate, for example derived from a buccal swab, paper, fabric or other substrate that may be impregnated with saliva, blood, or other bodily fluids. As such, in some embodiments, the nucleic acid sample may include low amounts of, or fragmented portions of DNA, such as genomic DNA. In some embodiments, target sequences can be present in one or more bodily fluids including but not limited to, blood, sputum, plasma, semen, urine, and serum. In some embodiments, target sequences can be obtained from hair, skin, tissue samples, autopsy, or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences or amplified target sequences are directed to purposes of human identification. In some embodiments, a method described herein can be used for identifying characteristics of a forensic sample. In some embodiments, a method described herein can be used for human identification methods using one or more target specific primers or one or more target specific primers designed using known primer design criteria. In one embodiment, a forensic or human identification sample containing at least one target sequence can be amplified using any one or more target-specific primers using known primer criteria.

Additional non-limiting examples of sources of biological samples can include whole organisms as well as a sample obtained from a patient. The biological sample can be obtained from any biological fluid or tissue and can be in a variety of forms, including liquid fluid and tissue, solid tissue, and preserved forms such as dried, frozen, and fixed forms. The sample may be of any biological tissue, cells, or fluid. Such samples include, but are not limited to, sputum, blood, serum, plasma, blood cells (e.g., white cells), ascitic fluid, urine, saliva, tears, sputum, vaginal fluid (discharge), washings obtained during a medical procedure (e.g., pelvic or other washings obtained during biopsy, endoscopy or surgery), tissue, nipple aspirate, core or fine needle biopsy samples, cell-containing body fluids, free floating nucleic acids, peritoneal fluid, and pleural fluid, or cells therefrom. Biological samples may also include sections of tissues such as frozen or fixed sections taken for histological purposes or micro-dissected cells or extracellular parts thereof. In some embodiments, the sample can be a blood sample, such as, for example, a whole blood sample. In another example, the sample is an unprocessed dried blood spot sample. In yet another example, the sample is a formalin-fixed paraffin-embedded sample. In yet another example, the sample is a saliva sample. In yet another example, the sample is a dried saliva spot sample.

Exemplary biological samples from which target nucleic acids can be derived include, for example, those from a eukaryote, for instance a mammal, such as a rodent, mouse, rat, rabbit, guinea pig, ungulate, horse, sheep, pig, goat, cow, cat, dog, primate, human or non-human primate; a plant, such as *Arabidopsis thaliana*, corn, sorghum, oat, wheat, rice, canola, or soybean; an algae, such as *Chlamydomonas reinhardtii*; a nematode such as *Caenorhabditis elegans*; an insect, such as *Drosophila melanogaster*, mosquito, fruit fly, honey bee or spider; a fish, such as zebrafish; a reptile; an amphibian, such as a frog or *Xenopus laevis*; a *Dictyostelium discoideum*; a fungi, such as *Pneumocystis carinii*, *Takifugu rubripes*, yeast, such as *Saccharamoyces cerevisiae* or *Schizosaccharomyces pombe*; or *Plasmodium falciparum*. Target nucleic acids can also be derived from a prokaryote such as a bacterium, *Escherichia coli*, staphylococci or *Mycoplasma pneumoniae*; an archaeon; a virus such as Hepatitis C virus or human immunodeficiency virus; or a viroid. Target nucleic acids can be derived from a homogeneous culture or population of organisms or alternatively from a collection of several different organisms, for example, in a community or ecosystem.

Random fragmentation refers to the fragmentation of a polynucleotide molecule from a primary nucleic acid sample in a non-ordered fashion by enzymatic, chemical, or mechanical methods. Such fragmentation methods are known in the art and use standard methods (Sambrook and Russell, Molecular Cloning, A Laboratory Manual, third edition). In one embodiment, fragmentation can be accomplished using a process often referred to as tagmentation. Tagmentation uses a transposome complex and combines into a single step fragmentation and ligation to add universal adapters (Gunderson et al., WO 2016/130704). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides comprising and/or surrounding the break. More particularly, the random fragmentation is by mechanical means such as nebulization or sonication to produce fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length Fragmentation of polynucleotide molecules by mechanical means (nebulization, sonication, and Hydroshear, for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

A population of target nucleic acids can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for a population of target nucleic acids can be in a range between a maximum and minimum value set forth herein. It will be understood that amplicons generated at an amplification site (or otherwise made or used herein) can have an average strand length that is in a range between an upper and lower limit selected from those exemplified above.

In some cases, a population of target nucleic acids can be produced under conditions or otherwise configured to have a maximum length for its members. For example, the maximum length for the members that are used in one or more steps of a method set forth herein or that are present in a particular composition can be less than 100,000 nucleotides, less than 50,000 nucleotides, less than 10,000 nucleotides, less than 5,000 nucleotides, less than 1,000 nucleotides, less than 500 nucleotides, less than 100 nucleotides, or less than 50 nucleotides. Alternatively or additionally, a population of target nucleic acids can be produced under conditions or otherwise configured to have a minimum length for its members. For example, the minimum length for the members that are used in one or more steps of a method set forth herein or that are present in a particular composition can be more than 10 nucleotides, more than 50 nucleotides, more than 100 nucleotides, more than 500 nucleotides, more than 1,000 nucleotides, more than 5,000 nucleotides, more than 10,000 nucleotides, more than 50,000 nucleotides, or more than 100,000 nucleotides. The maximum and minimum strand length for target nucleic acids in a population can be in a range between a maximum and minimum value set forth above. It will be understood that amplicons generated at an amplification site (or otherwise made or used herein) can have maximum and/or minimum strand lengths in a range between the upper and lower limits exemplified above.

In a particular embodiment, the target fragment sequences are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of a DNA molecule, for example, a PCR product. Such enzymes can be used to add a single nucleotide 'A' to the blunt ended 3' terminus of each strand of the double-stranded target fragments. Thus, an 'A' could be added to the 3' terminus of each end repaired strand of the double-stranded target fragments by reaction with Taq or Klenow exo minus polymerase, while the universal adapter polynucleotide construct could be a T-construct with a compatible 'T' overhang present on the 3' terminus of each region of double stranded nucleic acid of the universal adapter. This end modification also prevents self-ligation of both vector and target such that there is a bias towards formation of target nucleic acids having a universal adapter at each end.

In some cases, the target nucleic acids that are derived from such sources can be amplified prior to use in a method or composition herein. Any of a variety of known amplification techniques can be used including, but not limited to, polymerase chain reaction (PCR), rolling circle amplification (RCA), multiple displacement amplification (MDA), or random prime amplification (RPA). It will be understood that amplification of target nucleic acids prior to use in a method or composition set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof.

Universal Adapters

A target nucleic acid used in a method or composition described herein includes a universal adapter attached to each end. A target nucleic acid having a universal adapter at each end can be referred to as a "modified target nucleic acid." Methods for attaching a universal adapter to each end of a target nucleic acid used in a method described herein are known to the person skilled in the art. The attachment can be through standard library preparation techniques using ligation (U.S. Pat. Pub. No. 2018/0305753), or through tagmentation using transposase complexes (Gunderson et al., WO 2016/130704).

In one embodiment, double-stranded target nucleic acids from a sample, e.g., a fragmented sample, are treated by first ligating identical universal adaptor molecules ("mismatched adaptors," the general features of which are defined below, and further described in Gormley et al., U.S. Pat. No. 7,741,463, and Bignell et al., U.S. Pat. No. 8,053,192,) to the 5' and 3' ends of the double-stranded target nucleic acids. In one embodiment, the universal adaptor includes the universal capture binding sequences necessary for immobilizing the target nucleic acids on an array for subsequent sequencing. In another embodiment, a PCR step is used to further modify the universal adapter present at each end of target nucleic acids prior to immobilizing and sequencing. For instance, an initial primer extension reaction is carried out using a universal primer binding site in which extension products complementary to both strands of each individual target nucleic acid are formed and add a universal capture binding sequence. The resulting primer extension products, and optionally amplified copies thereof, collectively provide a library of modified target nucleic acids that can be immobilized and then sequenced. The term "library" refers to the collection of target nucleic acids containing known common sequences at their 3' and 5' ends, and may also be referred to as a 3' and 5' modified library.

The universal adapters used in the method of the disclosure are referred to as "mismatched" adaptors because, as is explained in detail herein, the adaptors include a region of sequence mismatch, i.e., they are not formed by annealing fully complementary polynucleotide strands.

Mismatched adaptors for use herein are formed by annealing two partially complementary polynucleotide strands to provide, when the two strands are annealed, at least one double-stranded region, also referred to as a region of double stranded nucleic acid, and at least one unmatched single-stranded region, also referred to as a region of single-stranded non-complementary nucleic acid strands.

The double-stranded region of the universal adapter is a short double-stranded region, typically including 5 or more consecutive base pairs, formed by annealing the two partially complementary polynucleotide strands. This term refers to a double-stranded region of nucleic acid in which the two strands are annealed and does not imply any particular structural conformation.

It is generally advantageous for the double-stranded region to be as short as possible without loss of function. In this context, "function" refers to the ability of the double-stranded region to form a stable duplex under standard reaction conditions for an enzyme-catalyzed nucleic acid ligation reaction, which will be well known to the skilled reader (e.g., incubation at a temperature in the range of 4° C. to 25° C. in a ligation buffer appropriate for the enzyme), such that the two strands forming the universal adapter remain partially annealed during ligation of the universal adapter to a target molecule. It is not absolutely necessary for the double-stranded region to be stable under the conditions typically used in the annealing steps of primer extension or PCR reactions.

The double-stranded region of the universal adapters is typically identical in all universal adapters used in a ligation. Because universal adapters are ligated to both ends of each target molecule, the modified target nucleic acid will be flanked by complementary sequences derived from the double-stranded region of the universal adapters. The longer the double-stranded region, and hence the complementary sequences derived therefrom in the modified target nucleic acid constructs, the greater the possibility that the modified target nucleic acid construct is able to fold back and base-pair to itself in these regions of internal self-complementarity under the annealing conditions used in primer extension and/or PCR. It is, therefore, generally preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

In one embodiment, the two strands of the universal adapter are 100% complementary in the double-stranded region. It will be appreciated that one or more nucleotide mismatches may be tolerated within the double-stranded region, provided that the two strands are capable of forming a stable duplex under standard ligation conditions.

Universal adaptors for use herein will generally include a double-stranded region forming the 'ligatable' end of the adaptor, e.g., the end that is joined to a double-stranded target nucleic acid in the ligation reaction. The ligatable end of the universal adaptor may be blunt or, in other embodiments, short 5' or 3' overhangs of one or more nucleotides may be present to facilitate/promote ligation. The 5' terminal nucleotide at the ligatable end of the universal adapter is typically phosphorylated to enable phosphodiester linkage to a 3' hydroxyl group on the target polynucleotide.

The term 'unmatched region' refers to a region of the universal adaptor, the region of single-stranded non-complementary nucleic acid strands, wherein the sequences of the two polynucleotide strands forming the universal adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for an enzyme-catalyzed ligation reaction, provided that the two strands revert to single stranded form under annealing conditions in an amplification reaction.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridize, and thus form a single stranded region on both strands. The mismatches may also take the form of 'bubbles', wherein both ends of the universal adapter construct(s) are capable of hybridizing to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this disclosure.

The lower limit on the length of the unmatched region will typically be determined by function, for example, the need to provide a suitable sequence for i) binding of a primer for primer extension, PCR and/or sequencing (for instance, binding of a primer to a universal primer binding site), or for ii) binding of a universal capture binding sequence to a capture nucleic acid for immobilization of a modified target nucleic acid to a surface. Theoretically there is no upper limit on the length of the unmatched region, except that in general it is advantageous to minimize the overall length of the universal adapter, for example, in order to facilitate separation of unbound universal adapters from modified target nucleic acid constructs following the ligation step. Therefore, it is generally preferred that the unmatched region should be less than 50, or less than 40, or less than 30, or less than 25 consecutive nucleotides in length.

The region of single-stranded non-complementary nucleic acid strands includes at least one universal capture binding sequence at the 3' end. The 3' end of a universal adapter includes a universal capture binding sequence that will hybridize to a capture nucleic acid present at amplification sites of an array. Optionally, the 5' end of a universal adapter includes a second universal capture binding sequence attached to each end of a target nucleic acid, where the second universal capture binding sequence will hybridize to a different capture nucleic acid present at amplification sites of an array.

The region of single-stranded non-complementary nucleic acid strands typically also includes at least one universal primer binding site. A universal primer binding site is a universal sequence that can be used for amplification and/or sequencing of a target nucleic acid ligated to the universal adapter.

The region of single-stranded non-complementary nucleic acid strands can also include at least one index. An index can be used as a marker characteristic of the source of particular target nucleic acids on an array (U.S. Pat. No. 8,053,192). Generally the index is a synthetic sequence of nucleotides that is part of the universal adapter which is added to the target nucleic acids as part of the library preparation step. Accordingly, an index is a nucleic acid sequence which is attached to each of the target molecules of a particular sample, the presence of which is indicative of, or is used to identify, the sample or source from which the target molecules were isolated. In one embodiment, a dual index system can be used. In a dual index system the universal adapter attached to target nucleic acids include two different index sequences (U.S. Pat. Pub. No. 2018/0305750, U.S. Pat. Pub. No. 2018/0305751, U.S. Pat. Pub. No. 2018/0305752, and U.S. Pat. Pub. No. 2018/0305753).

Preferably an index may be up to 20 nucleotides in length, more preferably 1-10 nucleotides, and most preferably 4-6 nucleotides in length. A four nucleotide index gives a possibility of multiplexing 256 samples on the same array, a six base index enables 4096 samples to be processed on the same array.

In one embodiment, the universal capture binding sequence is part of the universal adapter when it is ligated to the double-stranded target fragments, and in another embodiment the universal primer extension binding site is added to the universal adapter after the universal adapter is ligated to the double-stranded target fragments. The addition can be accomplished using routine methods, including amplification-based methods such as PCR.

The precise nucleotide sequence of the universal adapters is generally not material to the disclosure and may be selected by the user such that the desired sequence elements are ultimately included in the common sequences of the plurality of different modified target nucleic acids, for example, to provide for the universal capture binding sequences and binding sites for particular sets of universal amplification primers and/or sequencing primers. Additional sequence elements may be included, for example, to provide binding sites for sequencing primers which will ultimately be used in sequencing of target nucleic acids in the library, sequencing of an index, or products derived from amplification of the target nucleic acids in the library, for example on a solid support.

Although the precise nucleotide sequence of the universal adapter is generally non-limiting to the disclosure, the sequences of the individual strands in the unmatched region should be such that neither individual strand exhibits any internal self-complementarity which could lead to self-annealing, formation of hairpin structures, etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages.

Ligation and Amplification of Universal Adaptors

Ligation methods are known in the art and use standard methods. Such methods use ligase enzymes such as DNA ligase to effect or catalyze joining of the ends of the two polynucleotide strands of, in this case, the universal adapter and the double-stranded target nucleic acids, such that covalent linkages are formed. The universal adapter may contain a 5'-phosphate moiety to facilitate ligation to the 3'-OH present on the target fragment. The double-stranded target nucleic acid contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the disclosure, such joining takes place by formation of a phosphodiester linkage between the two polynucleotide strands, but other means of covalent linkage (e.g. non-phosphodiester backbone linkages) may be used.

As discussed herein, in one embodiment universal adaptors used in the ligation are complete and include a universal capture binding sequence and other universal sequences, e.g., a universal primer binding site and an index sequence. The resulting plurality of modified target nucleic acids can be used to prepare immobilized samples for sequencing.

Also as discussed herein, in one embodiment universal adaptors used in the ligation include a universal primer binding site and an index sequence, and do not include a universal capture binding sequence. The resulting plurality of modified target nucleic acids can be further modified to include specific sequences, such as a universal capture binding sequence. Methods for addition of specific sequences, such as a universal capture binding sequence, to universal primers that are ligated to double-stranded target fragments include amplification-based methods such as PCR, and are known in the art and are described in, for instance, Bignell et al. (U.S. Pat. No. 8,053,192) and Gunderson et al. (WO2016/130704).

In those embodiments where a universal adapter is modified, an amplification reaction is prepared. The contents of an amplification reaction are known by one skilled in the art and include appropriate substrates (such as dNTPs), enzymes (e.g. a DNA polymerase) and buffer components required for an amplification reaction. Generally, amplification reactions require at least two amplification primers, often denoted 'forward' and 'reverse' primers (primer oligonucleotides) that are capable of annealing specifically to a part of the polynucleotide sequence to be amplified, e.g., a modified target nucleic acid, under conditions encountered in the primer annealing step of each cycle of an amplification reaction. It will be appreciated that if the primers contain any nucleotide sequence which does not anneal to the modified target nucleic acids in the first amplification cycle then this sequence may be copied into the amplification products. For instance, the use of primers having universal capture binding sequences, e.g., sequences that do not anneal to the modified target nucleic acids, the universal capture binding sequences will be incorporated into the resulting amplicon.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand. Primers may additionally include non-nucleotide chemical modifications, for example phosphorothioates to increase exonuclease resistance, again provided such that modifications do not prevent primer function.

Amplification to Generate Clusters

An array that includes amplification sites, each of which includes a clonal population (also referred to as a cluster) of double stranded amplicons, can be produced using methods known to the person skilled in the art. In one embodiment, isothermal amplification methods are used, and include producing the clonal population of double stranded amplicons from an individual target nucleic acid that has seeded the site. In some embodiments the amplification reaction proceeds until a sufficient number of amplicons are generated to fill the capacity of the respective amplification site. Filling an already seeded site to capacity in this way excludes subsequent target nucleic acids from landing at the site, thereby producing a clonal population of amplicons at the site. Thus, it is desirable in some embodiments that the rate at which amplicons are generated to fill the capacity of amplification sites exceeds the rate at which the individual target nucleic acids are transported to the individual amplification sites.

In some embodiments, amplification methods include, but are not limited to, solid-phase amplification, polony amplification, colony amplification, emulsion PCR, bead RCA, surface RCA, or surface SDA. In some embodiments, amplification methods that results in amplification of free DNA molecules in solution or tethered to a suitable matrix by only one end of the DNA molecule are used. In some embodiments, methods that rely on bridge PCR, where both PCR primers are attached to a surface (see, e.g., WO 2000/018957, U.S. Pat. Nos. 7,972,820; 7,790,418 and Adessi et al., Nucleic Acids Research (2000): 28(20): E87) are used. In some embodiments the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). In some embodiments, methods are used that rely on kinetic exclusion, where recombinase-facilitated amplification and isothermal conditions amplify the library (U.S. Pat. Nos. 9,309,502, 8,895,249, 8,071,308).

In some embodiments, apparent clonality can be achieved even if an amplification site is not filled to capacity prior to a second target nucleic acid beginning amplification at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

Amplification sites in an array need not be entirely clonal in all embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons.

In some embodiments, the method of making an array useful in a method described herein can be carried out under conditions wherein the target nucleic acids are transported (e.g. via diffusion) to the amplification sites as amplification is occurring. Thus, some amplification methods can exploit both a relatively slow transport rate and a relatively slow production of a first amplicon relative to subsequent amplicon formation. For instance, an amplification reaction set forth herein can be carried out such that target nucleic acids are transported from solution to amplification sites simultaneously with (i) the producing of a first amplicon, and (ii) the producing of the subsequent amplicons at other sites of the array. In particular embodiments, the average rate at which the subsequent amplicons are generated at the amplification sites can exceed the average rate at which the target nucleic acids are transported from the solution to the amplification sites. In some cases, a sufficient number of amplicons can be generated from a single target nucleic acid at an individual amplification site to fill the capacity of the respective amplification site. The rate at which amplicons are generated to fill the capacity of respective amplification sites can, for example, exceed the rate at which the individual target nucleic acids are transported from the solution to the amplification sites.

A composition for amplifying target nucleic acids at amplification sites, referred to herein as an "amplification reagent," is typically capable of rapidly making copies of target nucleic acids at amplification sites. An amplification reagent used in a method of the present disclosure will generally include a polymerase and nucleotide triphosphates (NTPs). Any of a variety of polymerases known in the art can be used, but in some embodiments it may be preferable to use a polymerase that is exonuclease negative. Examples of nucleic acid polymerases suitable for use in embodiments of the present invention include, but are not limited to, DNA polymerase (such as Klenow fragment, T4 DNA polymerase, Bst (*Bacillus stearothermophilus*) polymerase), thermostable DNA polymerases (such as Taq, Vent, Deep Vent, Pfu, Tfl, and 9° N DNA polymerases) as well as their genetically modified derivatives (TaqGold, VENTexo, Pfu exo). In some embodiments, an amplification reagent can also include recombinase, accessory protein, and single-stranded DNA binding (SSB) protein for recombinase-facilitated amplification.

The NTPs can be deoxyribonucleotide triphosphates (dNTPs) for embodiments where DNA copies are made.

Typically the four native species, dATP, dTTP, dGTP and dCTP, will be present in a DNA amplification reagent; however, analogs can be used if desired. The NTPs can be ribonucleotide triphosphates (rNTPs) for embodiments where RNA copies are made. Typically the four native species, rATP, rUTP, rGTP and rCTP, will be present in a RNA amplification reagent; however, analogs can be used if desired. NTPs can be modified with a fluorescent or radioactive group. A large variety of synthetically modified nucleic acids have been developed for chemical and biological methods in order to increase the detectability and/or the functional diversity of nucleic acids. These functionalized/modified molecules (e.g., nucleotide analogs) can be fully compatible with natural polymerizing enzymes, maintaining the base pairing and replication properties of the natural counterparts.

Other components of the amplification solution are added consequently to the choice of the polymerase, and they are essentially corresponding to compounds known in the art as being effective to support the activity of each polymerase. The concentration of compounds like dimethyl sulfoxide (DMSO), Bovine Serum Albumin (BSA), poly-ethylene glycol (PEG), Betaine, Triton X-100, denaturant (e.g., formamide), or $MgCl_2$ is well known in the prior art as being important to have an optimal amplification, and therefore the operator can easily adjust such concentrations for the methods of the present disclosure on the basis of the examples presented hereafter and the knowledge generally available.

The rate at which an amplification reaction occurs can be increased by increasing the concentration or amount of one or more of the active components of an amplification reaction. For example, the amount or concentration of polymerase, nucleotide triphosphates, or primers. In some cases, the one or more active components of an amplification reaction that are increased in amount or concentration (or otherwise manipulated in a method set forth herein) are non-nucleic acid components of the amplification reaction.

Amplification rate can also be increased in a method set forth herein by adjusting the temperature. For example, the rate of amplification at one or more amplification sites can be increased by increasing the temperature at the site(s) up to a maximum temperature where reaction rate declines due to denaturation or other adverse events. Optimal or desired temperatures can be determined from known properties of the amplification components in use or empirically for a given amplification reaction mixture. Such adjustments can be made based on a priori predictions of primer melting temperature ($T_m$) or empirically. In certain embodiments the temperature of an amplification reaction are at least 35° C. to no greater than 70° C. For instance, an amplification reaction can be at least 35° C. to no greater than 42° C., or at least 57° C. to no greater than 63° C.

The rate at which an amplification reaction occurs can be increased by increasing the activity of one or more amplification reagent. For example, a cofactor that increases the extension rate of a polymerase can be added to a reaction where the polymerase is in use. In some embodiments, metal cofactors such as magnesium, zinc, or manganese can be added to a polymerase reaction or betaine can be added.

Preparation of Immobilized Samples for Sequencing

The result of bridging amplification is a population of clonal "bridged" amplification products at the amplification sites. Both strands of the amplicon acid are immobilized on the surface of an amplification site at the 5' ends, where this attachment is derived from the original attachment of the capture nucleic acids (for instance, see FIG. 1A where a double-stranded amplicon 11 is depicted in a "bridged" orientation). The amplicons within amplification sites will be clonal and derived from amplification of a single target nucleic acid, or with acceptable levels of another amplicon as described herein.

A large number of unused capture nucleic acids remain on the surface of the amplification site after amplification to form a clonal cluster of bridged amplification products, in addition to the free 3'-ends of each of the strands of the bridged double stranded amplicons. The presence of the unused capture nucleic acids can contribute to increased noise, and are therefore typically removed by contacting the array with a nuclease under conditions suitable for the nuclease to digest the unused capture nucleic acids. In one embodiment, the nuclease is an exonuclease, such as an exonuclease having a 3' to 5' single-stranded DNA exonuclease activity. An example of such an exonuclease is exonuclease I. Nuclease treatment is followed by washing the array to remove the nuclease and resulting nucleotides and/or nucleic acids from the amplification sites.

To facilitate sequencing, one of the strands of the double stranded bridged structure can be selectively removed from the surface to allow efficient hybridization of a sequencing primer to the remaining immobilized strand. The selective removal of a specific strand is referred to herein as "linearization." Examples of suitable methods for linearization are described herein and are described in more detail in application number WO 2007/010251 and U.S. Pat. Application Pub. 2012/0309634.

In one embodiment, linearization is achieved by cleaving one strand of the bridged double stranded amplicons and then subjecting the resulting structure to conditions that remove the strand that is no longer attached to the amplification site surface. Cleavage can be accomplished through the use of a capture nucleic acid that includes a cleavage site. The cleavage site is typically in a location that results in a substantial portion of one strand of the bridged structure to be free of the surface of the amplification site—no longer immobilized—and susceptible to loss after the removal step. For instance, as shown in FIG. 1B, the cleavage site X in the amplicon 11 is cleaved leaving a shortened capture nucleic acid 13". One strand 16 of the bridged structure remains immobilized at its 5' end to the amplification site 10, and the other strand 15' is no longer immobilized due to the cleavage at X. In one embodiment, the 3' end of strand 16 remains annealed to complementary bases of the shortened capture nucleic acid 13", thereby maintaining the bridge structure after linearization. The number of complementary bases between the 3' end of strand 16 and the shortened capture nucleic acid 13" that maintain the bridge structure varies depending upon the prevalent conditions, and can be determined by the skilled person.

In one embodiment, a cleavage site is treated to remove a nucleotide and make an abasic site. An "abasic site" is a nucleotide position in a nucleic acid from which the base component has been removed. Abasic sites can be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a nucleic acid.

In one embodiment, an abasic site may be created at a pre-determined position on one strand of an immobilized amplicon. This can be achieved, for example, by incorporating a specific nucleotide at the pre-determined position.

In one embodiment, a deoxyuridine (U) is incorporated in one of the capture nucleic acids attached to the surface of an amplification site. The enzyme uracil DNA glycosylase (UDG) can then be used to remove the uracil base, generating an abasic site on one strand. The polynucleotide strand including the abasic site can then be cleaved at the abasic site by treatment with endonuclease (e.g., DNA glycosylase-lyase Endonuclease VIII), heat or alkali. In a particular embodiment, the USER reagent available from New Englad Biolabs (NEB # M5505S) is used for the creation of a single nucleotide gap at a uracil base in an immobilized. In one embodiment, the amplification sites are exposed to a mixture containing the appropriate glycosylase and one or more suitable endonucleases, typically in an activity ratio of at least about 2:1. Treatment with endonuclease enzymes gives rise to a 3'-phosphate moiety at the cleavage site, which can be removed with a suitable phosphatase such as alkaline phosphatase. For instance, as shown in FIG. 1B, if the cleavage site X is produced using the USER reagent the shortened capture nucleic acid 13" will terminate with a 3'-phosphate group.

In one embodiment, an 8-oxo-guanine is incorporated in one of the capture nucleic acids attached to the surface of an amplification site. The enzyme FPG glycosylase can then be used to remove the 8-oxo-guanine base, generating an abasic site on one strand. In another embodiment, a deoxyinosine is incorporated in one of the capture nucleic acids attached to the surface of an amplification site, and the enzyme AlkA glycosylase can then be used to remove the deoxyinosine base, generating an abasic site on one strand.

Advantages of this method include the option of releasing a free 3' phosphate group on the cleaved strand, which after phosphatase treatment can provide an initiation point for sequencing a region of the complementary strand (for instance, sequencing a region of strand 16 of FIG. 1B). Because the cleavage reaction requires a residue, e.g., deoxyuridine, which does not occur naturally in DNA, but is otherwise independent of sequence context, if only one non-natural base is included there is no possibility of glycosylase-mediated cleavage occurring elsewhere at unwanted positions in the duplex. Another advantage gained by cleavage of abasic sites in a double-stranded section of an immobilized amplicon generated by action of UDG on uracil is that the first base incorporated in a sequencing-by-synthesis reaction initiating at the free 3' hydroxyl group formed by cleavage will always be T. As a result, for all clonal clusters at different amplification sites of an array which are cleaved in this manner to produce sequencing templates the first base universally incorporated across the whole array will be T. This can provide a sequence-independent assay for individual cluster intensity at the start of a sequencing run.

The steps of adding exonuclease and linearization are known to the person skilled in the art as necessarily being separate steps. Treatment with endonuclease enzymes gives rise to a 3'-phosphate moiety at the cleavage site, and the presence of 3' phosphate is known to inhibit the activity of exonuclease I (Lehman and Nussbaum, 1964, J. Biol. Chem., 239: 2628-2636). The inventors made the unexpected and surprising discovery that both exonuclease and linearization steps can occur at the same time by combining the enzymes. The reduction of these two steps into one results in faster sequencing runs as two steps are now preformed simultaneously. Moreover, combining both steps does not have a detrimental effect on primary metrics, read quality, dual indexing, or genome build metrics.

Abasic site generation and cleavage results in a free 5'-end on the strand that is no longer immobilized to the surface (for instance, as shown in FIG. 1B, one strand 16 of the bridged structure remains immobilized at its 5' end to the amplification site 10, and the other strand 15' is no longer immobilized due to the cleavage at X). This strand can be completely removed from the surface by exposing the amplification site to suitable conditions. In one embodiment, removal is by denaturation. The denaturation can be performed thermally or isothermally, for example using chemical denaturation. The chemical denaturant may be urea, hydroxide, or formamide or other similar reagent. In another embodiment, removal can be achieved by treatment with an exonuclease with 5'-3' activity, such as lambda or T7 exonuclease. Removal of the unattached strand results in a remaining single strand that can act as a template for a polymerase.

Optionally, the 3' ends of the nucleic acids at the amplification sites are repaired. The exonuclease can remove some of the nucleotides at the 3' ends of the nucleic acids after the linearization. Without intending to be limiting, it is possible the 3' ends are "breathing" slightly resulting in a small number of nucleotides becoming single stranded and available to the exonuclease for digestion. Repair can be achieved by exposing the nucleotides to a DNA polymerase, such as the DNA polymerase used for the bridging amplification.

Removal of the unattached strand is optional. In one embodiment, the 3'-phospate group remaining after generation of the abasic site is removed to leave a 3'-hydroxyl group at the end of the cleaved capture nucleic acid (FIG. 1B, shortened capture nucleic acid 13". This capture nucleic acid can be used as a primer for a polymerase with strand displacing activity. As the polymerase uses the immobilized strand (FIG. 1B, strand 16) as a template to synthesize the complementary strand it displaces the unattached strand (FIG. 1B, strand 15').

Compositions

During or following an amplification clustering method described herein different compositions can result. In one embodiment, a composition includes a glycosylase, an endonuclease, and an exonuclease. In one embodiment, the exonuclease has a 3' to 5' single-stranded DNA exonuclease activity, such as exonuclease I. In one embodiment, one type of glycosylase that can be present in the composition is uracil DNA glycosylase, and the endonuclease is DNA glycosylase-lyase Endonuclease VIII. In one embodiment, one type of glycosylase that can be present in the composition is FPG glycosylase, and the endonuclease is DNA glycosylase-lyase Endonuclease VIII. In one embodiment, one type of glycosylase that can be present in the composition is AlkA glycosylase, and the endonuclease is DNA glycosylase-lyase Endonuclease VIII. The composition can include a double-stranded DNA substrate that includes a uracil cleavage site, an 8-oxo-guanine cleavage site, or a deoxyinosine cleavage site. The composition can include a double-stranded DNA substrate that includes an abasic site. In some embodiments, the composition the double-stranded DNA substrate can include a single-stranded region, where the uracil cleavage site and the abasic site are present in the double-stranded region. Also provided is an array that includes a plurality of amplification sites, where each amplification site includes a plurality of the double-stranded DNA substrates attached to the amplification sites.

Use in Sequencing/Methods of Sequencing

An array of the present disclosure, having been produced by a method set forth herein and including amplified and linearized amplicons at amplification sites, can be used for any of a variety of applications. A particularly useful application is nucleic acid sequencing. One example is sequencing-by-synthesis (SBS). In SBS, extension of a nucleic acid primer along a nucleic acid template (e.g., a target nucleic acid or amplicon thereof) is monitored to determine the sequence of nucleotides in the template. The underlying chemical process can be polymerization (e.g., as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates at different sites of an array set forth herein can be subjected to an SBS technique under conditions where events occurring for different templates can be distinguished due to their location in the array.

Flow cells provide a convenient format for housing an array that is produced by the methods of the present disclosure and that is subjected to an SBS or other detection technique that involves repeated delivery of reagents in cycles. For example, to initiate a first SBS cycle, one or more labeled nucleotides, DNA polymerase, etc., can be flowed into/through a flow cell that houses an array of nucleic acid templates. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123,744; U.S. Pat. Nos. 7,329,492; 7,211, 414; 7,315,019; 7,405,281, and 8,343,746.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence-based detection systems are not necessary for pyrosequencing procedures. Useful fluidic systems, detectors and procedures that can be used for application of pyrosequencing to arrays of the present disclosure are described, for example, in WIPO Published Pat. App. 2012/058096, US 2005/0191698 A1, U.S. Pat. Nos. 7,595,883, and 7,244,559.

Sequencing-by-ligation reactions are also useful including, for example, those described in Shendure et al. Science 309:1728-1732 (2005); U.S. Pat. Nos. 5,599,675; and 5,750, 341. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977. In both sequencing-by-ligation and sequencing-by-hybridization procedures, template nucleic acids (e.g., a target nucleic acid or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can use methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008).

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/ 0026082 A1; US 2009/0127589 A1; US 2010/0137143 A1; or US 2010/0282617 A1. Methods set forth herein for amplifying target nucleic acids can be readily applied to substrates used for detecting protons. More specifically, methods set forth herein can be used to produce clonal populations of amplicons at the sites of the arrays that are used to detect protons.

A useful application for an array of the present disclosure, for example, having been produced by a method set forth herein, is gene expression analysis. Gene expression can be detected or quantified using RNA sequencing techniques, such as those referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1.

Another useful application for an array having been produced by a method set forth herein is single-cell sequencing. When combined with indexing methods single cell sequencing can be used in chromatin accessibility assays to produce profiles of active regulatory elements in thousands of single cells, and single cell whole genome libraries can be produced. Examples for single-cell sequencing that can be carried out on an array of the present disclosure are described in U.S. Published Patent Application 2018/0023119 A1, U.S. Provisional Application Ser. No. 62/673,023 and Ser. No. 62/680,259.

An advantage of the methods set forth herein is that they provide for rapid and efficient creation of arrays from any of a variety of nucleic acid libraries. Accordingly the present disclosure provides integrated systems capable of making an array using one or more of the methods set forth herein and further capable of detecting nucleic acids on the arrays using techniques known in the art such as those exemplified herein. Thus, an integrated system of the present disclosure can include fluidic components capable of delivering amplification reagents to an array of amplification sites such as pumps, valves, reservoirs, fluidic lines and the like. A particularly useful fluidic component is a flowcell. A flowcell can be configured and/or used in an integrated system to create an array of the present disclosure and to detect the array. Exemplary flow cells are described, for example, in US 2010/0111768 A1 and U.S. Pat. No. 8,951,781. As exemplified for flowcells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those described herein. Alternatively, an integrated system can include separate fluidic systems to carry out amplification methods and to carry out detection methods. Examples of integrated sequencing systems that are capable of creating arrays of nucleic acids and also determining the sequence of the nucleic acids include, without limitation, the MiSeq™, HiSeq2500™, NextSeq™, MiniSeq™, NovaSeq™ and iSeq™ sequencing platforms from Illumina, Inc. (San Diego, Calif.) and devices described in U.S. Pat. No. 8,951,781. Such devices can be modified to make arrays in accordance with the guidance set forth herein.

A system capable of carrying out a method set forth herein need not be integrated with a detection device. Rather, a stand-alone system or a system integrated with other devices is also possible. Fluidic components similar to those exemplified above in the context of an integrated system can be used in such embodiments.

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating an array under bridge amplification conditions. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

It will be understood that an array of the present disclosure, for example, having been produced by a method set forth herein, need not be used for a detection method. Rather, the array can be used to store a nucleic acid library. Accordingly, the array can be stored in a state that preserves the nucleic acids therein. For example, an array can be stored in a desiccated state, frozen state (e.g. in liquid nitrogen), or in a solution that is protective of nucleic acids. Alternatively or additionally, the array can be used to replicate a nucleic acid library. For example, an array can be used to create replicate amplicons from one or more of the sites on the array.

Referring now to FIG. 1A, a schematic is shown of an amplification site 10 with one member of a plurality of double-stranded amplicons 11. The depicted double-stranded amplicon 11 includes a first strand 15 and a second strand 16. Also shown are two populations of capture nucleic acids. A first population is shown either attached 13 at one end of the first strand 15, or bound 13' to the surface of the amplification site 10. A second population of capture nucleic acids is also shown either attached 14 at the one end of the second strand 16, or bound 14' to the surface of the amplification site 10. Also shown in FIG. 1A is the cleavage site (marked with an X on capture nucleic acid 13). In one embodiment, a capture nucleic acid 13 can include a P5 capture nucleic acid and the other capture nucleic acid 14 can include a P7 capture nucleic acid.

FIG. 1B shows cleavage of the cleavage site X in the capture nucleic acid 13 attached to the first strand. The cleavage of capture nucleic acid 13 results in (i) a shortened strand 15' and (ii) a shortened capture nucleic acid 13". The shortened strand 15' is no longer attached to the amplification site 10. The shortened capture nucleic acid 13" can end with a 3' phosphate. In the depicted embodiment, nucleotides present at the 3' end of the strand 16 remain annealed to nucleotides present at the 3' end of the shortened capture nucleic acid 13". The unattached capture nucleic acids 13' and 14' are no longer present at the amplification site 10 due to the action of an exonuclease, such as exonuclease I.

FIG. 1C shows the result of exposing the amplicon of FIG. 1B to denaturing conditions. The shortened strand 15' that is not attached to the amplification site 10 is removed from the strand 16, and the nucleotides at the 3' end of strand 16 are not annealed to nucleotides present at the 3' end of the shortened capture nucleic acid 13".

FIG. 1D shows the result of re-annealing. The attached stand 16 is re-annealed to the shortened capture nucleic acid 13".

EXEMPLARY EMBODIMENTS

Embodiment 1

A composition comprising:
uracil DNA glycosylase,
an endonuclease, and
an exonuclease comprising a 3' to 5' single-stranded DNA exonuclease activity.

Embodiment 2

The composition of Embodiment 1, wherein the exonuclease is exonuclease I.

Embodiment 3

The composition of Embodiments 1 or 2, wherein the endonuclease is DNA glycosylase-lyase Endonuclease VIII.

Embodiment 4

The composition of any one of Embodiments 1-3, further comprising a double-stranded DNA substrate that comprises a uracil cleavage site.

Embodiment 5

The composition of any one of Embodiments 1-4, further comprising a double-stranded DNA substrate that comprises an abasic site.

Embodiment 6

The composition of any one of Embodiments 1-5, wherein the double-stranded DNA substrate comprises a single-stranded region, and wherein the uracil cleavage site and the abasic site are present in the double-stranded region.

Embodiment 7

The composition of any one of Embodiments 1-6, further comprising an array comprising a plurality of amplification sites, wherein each amplification site comprises a plurality of the double-stranded DNA substrates attached to the amplification sites.

Embodiment 8

A method of preparing nucleic acids for a sequencing reaction, the method comprising:
(a) providing an array comprising a plurality of amplification sites, wherein amplification sites comprise
   (i) a plurality of capture nucleic acids attached to the amplification sites,
      wherein a first population of the plurality of capture nucleic acids comprises a cleavage site, and
   (ii) a plurality of clonal double-stranded modified target nucleic acids,
      wherein both strands of each double-stranded target nucleic acid are attached at their 5' ends to a capture nucleic acid,
      wherein one strand is attached to a capture nucleic acid that comprises the cleavage site, and
      wherein the cleavage site is positioned in a double-stranded region of each double-stranded molecule;
(b) contacting the array with a composition comprising at least one enzyme to produce an abasic site at the cleavage site and an exonuclease comprising a 3' to 5' single-stranded DNA exonuclease activity,
   wherein cleavage occurs at the cleavage site,
   wherein cleavage converts one strand of double-stranded target nucleic acids into a first strand attached to the amplification site and a second strand that is not attached to the amplification site; and wherein single-stranded capture nucleic acids comprising a free 3' end are reduced in length by the exonuclease.

Embodiment 9

The method of Embodiment 8, wherein the at least one enzyme to produce an abasic site at the cleavage site comprises uracil DNA glycosylase and an endonuclease.

Embodiment 10

The method of Embodiment 8 or 9, wherein the endonuclease is DNA glycosylase-lyase Endonuclease VIII.

Embodiment 11

The method of any one of Embodiments 8-10, further comprising removal of the at least one enzyme to produce an abasic site at the cleavage site and the exonuclease from the array.

Embodiment 12

The method of any one of Embodiments 8-11, further comprising subjecting the cleaved double-stranded target nucleic acids to conditions that remove the second strand that is not attached to the amplification site.

Embodiment 13

The method of Embodiment 8-12, wherein the conditions that remove the second strand comprise a denaturant, wherein the denaturant results in immobilized single-stranded nucleic acids comprising a target nucleic acid covalently attached to a second population of capture nucleic acid, wherein the second population of capture nucleic acids is attached to the amplification sites.

Embodiment 14

The method of any one of Embodiments 8-13, wherein the denaturant comprises formamide.

Embodiment 15

The method of any one of Embodiments 8-14, further comprising re-annealing the immobilized single-stranded nucleic acid to a member of the first population of capture nucleic acids to generate an immobilized partially single-stranded nucleic acids.

Embodiment 16

The method of any one of Embodiments 8-15, wherein the cleavage site is positioned in the capture nucleic acid region of the double-stranded region of each double-stranded target nucleic acid.

Embodiment 17

The method of any one of Embodiments 8-16, wherein the cleavage site comprises a uracil, wherein an abasic site is generated by the uracil DNA glycosylase, and wherein the abasic site is cleaved by the endonuclease.

Embodiment 18

The method of any one of Embodiments 8-17, wherein the exonuclease is Exonuclease I.

Embodiment 19

The method of any one of Embodiments 8-18, further comprising hybridizing a sequencing primer to the immobilized single-stranded nucleic acids of Embodiment 13 or a single stranded region of the immobilized partially single-stranded nucleic acids of Embodiment 15, thereby preparing single-stranded nucleic acids for a sequencing reaction.

Embodiment 20

The method of any one of Embodiments 8-19, further comprising performing a sequencing reaction to determine the sequence of at least one region of the immobilized single-stranded nucleic acids or the immobilized partially single-stranded nucleic acids.

Embodiment 21

The method of any one of Embodiments 8-20, wherein the sequencing reaction comprises sequencing-by-synthesis.

Embodiment 22

The method of any one of Embodiments 8-21, wherein the array is produced by amplifying a plurality of target nucleic acids using the capture nucleic acids as amplification primers.

Embodiment 23

The method of any one of Embodiments 8-22, wherein amplifying comprises exclusion amplification.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

General Assay Methods and Conditions

Unless otherwise noted, this describes the general assay conditions used in the Examples described herein.

Experiments were run using v2.5 HiSeqX flowcells (ILMN) on a cBot (ILMN). For FIG. 2 the flowcell was used without amplification of clusters, using the P5 and P7 surface primers as a substrate to test for enzymatic activity. During the experiment various enzyme mixes were pumped into the flowcell and incubated at 37° C. for 15 mins. Exonuclease I and USER enzymes were both supplied by New England Biolabs. After incubation the flowcell lanes were washed with HT2 wash buffer (Illumina) and then presence or absence of surface primers determined via hybridization of fluorophore TET-labelled P5' and P7' oligos, in HT1 hybridisation buffer (Illumina). Fluorescent signal was detected by scanning on a Typhoon flatbed imager (GE Healthcare Life Sciences).

Figure 3:
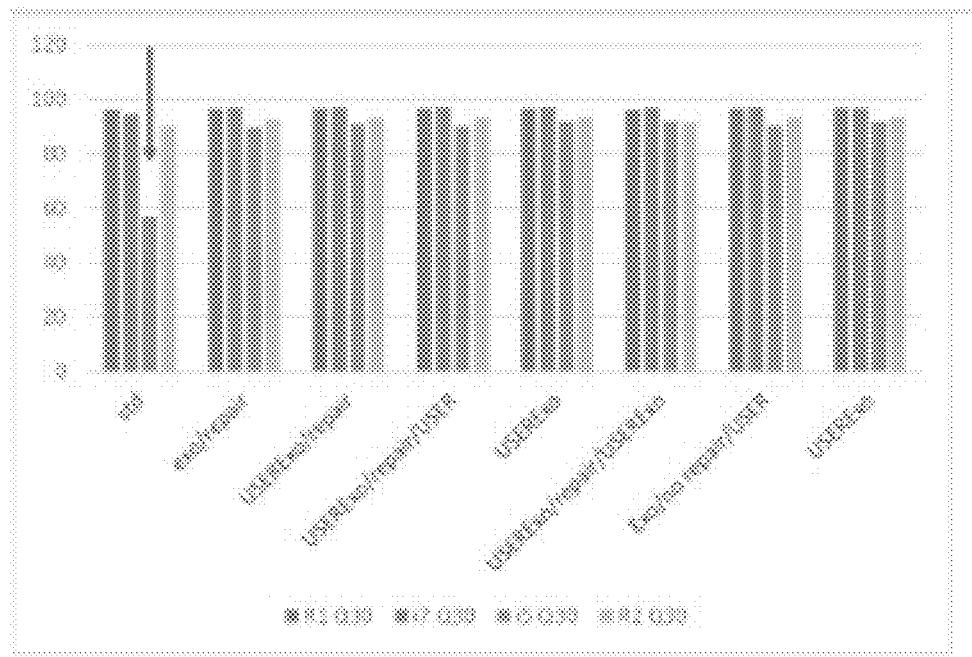
FIG. 3 shows the results of the sequencing runs as described in Examples 1 and 3.

For FIG. 3, cluster seeding and amplification was achieved by mixing denatured DNA templates (human TruSeq Nano library) to a final concentration of 300 pM in ExAmp mix, and this was pumped into the flowcell and incubated for 1 hour at 37° C. Different lanes of the flowcell were then processed with different combinations of enzymes and treatments as detailed in the chart. "Repair" refers to the 3 cycles of bridge amplification which are usually done to fill-in the ends of strands which can become nibbled during the exonuclease step. "USEREXo" refers to the combined mix of USER and ExoI. After these steps, the clusters were hybridized with sequencing primer and sequenced on a HiSeqX using standard methods and reagents (ILMN).

Example 2

Exonuclease and Linearization Reactions can be Combined

Standard methods for generating clusters that can be used for genomic sequencing include hybridizing target nucleic acids to a cluster, amplifying the target nucleic acids, and then treatment of a cluster with exonuclease I to remove excess free surface primers. In a separate step the immobilized strands are then linearized by generating a single nucleotide gap in a specific region of double stranded DNA (dsDNA) to produce templates for sequencing. We tested whether the exonuclease and linearization steps could be combined. Lanes of a flowcell with amplification sites having attached surface primers were treated with exonuclease 1, the enzymes that generate a single nucleotide gap in a specific region of dsDNA (a combination of uracil DNA glycosylase and DNA glycosylase-lyase Endonuclease VIII), or the combination of both.

Figure 2:
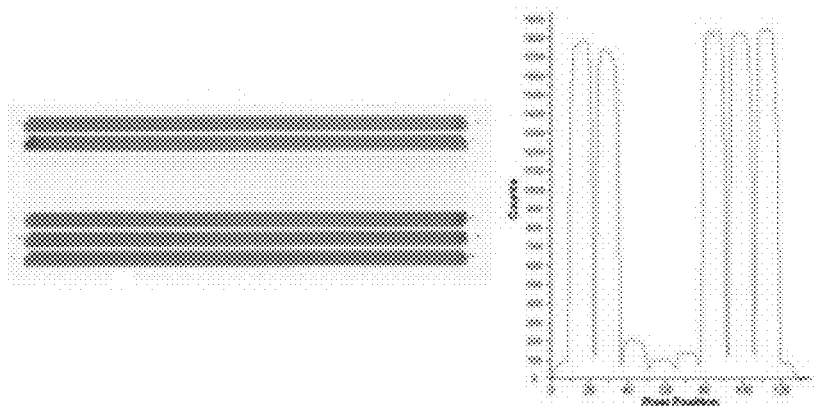
FIG. 2 shows the effect of 3'-phosphate and DNA glycosylases on Exonuclease I activity. The left panel shows the presence of the DNA glycosylases and the exonuclease in each lane of a flowcell. The DNA glycosylases were added first, followed by addition of the exonuclease. The exception is lane 4, where the DNA glycosylases and the exonuclease were added simultaneously. The middle panel shows a flowcell with lanes 1-8 numbered from top to bottom, and the absence of signal in lanes 3-5. The right panel shows the results in fluorescence of the lanes, where lanes 3-5 have essentially no fluorescence.

FIG. 2 shows that no treatment (lanes 1 and 8) or treatment with uracil DNA glycosylase and DNA glycosylase-lyase Endonuclease VIII (lane 2) resulted in no loss of surface primers, while treatment with exonuclease I (lane 5) resulted in loss of essentially all surface primers. Treatment with uracil DNA glycosylase and DNA glycosylase-lyase Endonuclease VIII followed by exonuclease I (lane 3) and treatment with a mixture of exonuclease combined with uracil DNA glycosylase and DNA glycosylase-lyase Endonuclease VIII (lane 4) resulted in loss of essentially all surface primers. This was unexpected and surprising, because treatment of dsDNA with a combination of uracil DNA glycosylase and DNA glycosylase-lyase Endonuclease VIII results in 3' phosphates, and the presence of 3' phosphate is known to inhibit the activity of exonuclease I (Lehman and Nussbaum, 1964, J. Biol. Chem., 239: 2628-2636).

Example 3

Simultaneous Exonuclease Treatment and Linearization Results in Templates that are Useful for Sequencing To determine if simultaneous use of DNA glycosylases and exonuclease had any detrimental effect on sequencing metrics, sequencing runs were made on flowcells containing clusters generated using different combinations of DNA glycosylases and exonuclease. The quality score of each run was determined in quadruplicate and is shown in FIG. 3. As expected, the standard lane (no exonuclease and no repair) which included the sequence reaction with a lawn of P5 primers had Q30 values in the mid-50s (see arrow, FIG. 3). All other lanes were approximately equivalent, and those reactions using the DNA glycosylases and the exonuclease in a single step resulted in the best R2 reads with a Q30 of approximately 93%.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A composition comprising:
a uracil DNA glycosylase;
an endonuclease;
an exonuclease comprising a 3' to 5' single-stranded DNA exonuclease activity, and
an array comprising a plurality of amplification sites.

2. The composition of claim 1, wherein the exonuclease is exonuclease I.

3. The composition of claim 1, wherein the endonuclease is DNA glycosylase-lyase Endonuclease VIII.

4. The composition of claim 1, wherein each amplification site comprises a plurality of double-stranded DNA substrates attached to the amplification site, wherein the double-stranded DNA substrates comprise a uracil cleavage site.

5. The composition of claim 1, wherein each amplification site comprises a plurality of double-stranded DNA substrates attached to the amplification site, wherein the double-stranded DNA substrates comprise an abasic site.

6. The composition of claim 4, wherein the double-stranded DNA substrate comprises a single-stranded region, and wherein the uracil cleavage site is present in the double-stranded region.

7. The composition of claim 5, wherein the double-stranded DNA substrate comprises a single-stranded region, and wherein the abasic site is present in the double-stranded region.

* * * * *